(12) United States Patent
Granoff

(10) Patent No.: US 6,413,520 B1
(45) Date of Patent: Jul. 2, 2002

(54) METHODS OF IMMUNIZING ADULTS USING ANTI-MENINGOCOCCAL VACCINE COMPOSITIONS

(75) Inventor: Dan Granoff, Berkeley, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/446,347

(22) PCT Filed: Jun. 24, 1998

(86) PCT No.: PCT/US98/13080
§ 371 (c)(1),
(2), (4) Date: Dec. 16, 1999

(87) PCT Pub. No.: WO98/58670
PCT Pub. Date: Dec. 30, 1998

Related U.S. Application Data

(60) Provisional application No. 60/050,581, filed on Jun. 24, 1997.

(51) Int. Cl.$^7$ .............................................. A61K 39/385
(52) U.S. Cl. ................. 424/197.11; 424/194.1; 424/250.1; 514/2; 514/8; 530/403
(58) Field of Search .............................. 424/92, 197.11, 424/194.1, 250.1; 514/2, 8; 530/403, 405, 411, 807

(56) References Cited

U.S. PATENT DOCUMENTS

| 4,727,136 A | | 2/1988 | Jennings et al. |
| 5,425,946 A | * | 6/1995 | Tai et al. ............... 424/197.11 |

FOREIGN PATENT DOCUMENTS

| EP | 0 504 202 B1 | 5/1995 |
| WO | WO 94/05325 | 3/1994 |
| WO | WO 98/08543 | 3/1998 |

OTHER PUBLICATIONS

MMWR (Morbidity and Mortality Weekly Report, , vol. 46 (RR–5) pp. 1–10), Feb. 1997.*

Anderson et al. (Infection and Immunity, vol. 62, No. 8, pp. 3391–3395), Aug. 1994.*

Braude, A.I., "Medical Microbiology and Infectious Diseases". 1981 W.B. Saunders Company, 1981.*

MMWR (Morbidity and Mortality Weekly Report, May 10, 1985, vol. 34 No. 18, pp. 255–259), May 1985.*

Brandt, et al., "Duration of Antibody Responses after Vaccination with Group C *Neisseria meningitidis* Polysaccharide," *J. Infect. Dis.* 131:S69–S72 (1975).

Granoff, et al., "Induction of Immunologic Refractoriness in Adults by Meningococcal C Polysaccharide Vaccination," *J. Infect. Dis.* 178:870–874 (1998).

Granoff, et al., "Induction of immunologic tolerance in adults by meningococcal C (MenC) polysaccharide (PS) vaccination," *Clinical Infectious Diseases* 25(2):432 / A417 (1997).

King, et al., "3 year follow–up and booster response to quadrivalent meninococcal polysaccharide vaccine (QMPV)," *Pediatric Res.* 39(2): 106 / A62 (1996).

* cited by examiner

*Primary Examiner*—Donna C. Wortman
*Assistant Examiner*—Robert A. Zeman
(74) *Attorney, Agent, or Firm*—Roberta L. Robins; Alisa A. Harbin; Robert P. Blackburn

(57) ABSTRACT

A method for boosting an immune response against meningococcal capsular antigen is disclosed. The method entails administering a first glycoconjugate vaccine composition to a subject to provide an initial state of anti-meningococcal immunity, and then boosting the anti-meningococcal immunity by administration of a second, boosting vaccination. Also disclosed is the use of vaccine compositions in the preparation of anti-meningococcal medicaments. The use entails administering a first glycoconjugate vaccine composition to a subject to provide an initial state of anti-meningococcal immunity, and then boosting the anti-meningococcal immunity by administration of a second, boosting vaccination.

8 Claims, 1 Drawing Sheet

METHODS OF IMMUNIZING ADULTS USING ANTI-MENINGOCOCCAL VACCINE COMPOSITIONS

CROSS-REFERENCE TO RELATED APPLICATION

This application is related to provisional patent application Ser. No. 60/050,581, filed Jun. 24, 1997, from which priority is claimed under 35 U.S.C. §119 (e) (1) and which is incorporated herein by reference in its entirety.

FIELD OF THE INVENTION

The present invention relates to methods for immunizing a subject against meningococcal disease. More particularly, the invention relates to a method for avoiding immunological tolerance against meningococcal species in vaccinated subjects, using an anti-meningococcal glycoconjugate vaccine composition as the primary immunogen.

BACKGROUND OF THE INVENTION

*Neisseria meningitidis* is an important cause of invasive bacterial disease, with an estimated 2600 cases of meningococcal meningitis occurring in the United States each year, primarily in children and young adults (Jafari et al. (1997) *MMWR* 46:1–10; Perkins et al. (1997) *MMWR* 46:13–21). In England and Wales, there has been a steady rise in reported cases of meningococcal disease since 1984, peaking at greater than 2000 cases per year in 1991 and 1992 (Jones, D. (1995) "Epidemiology of Meningococcal Disease in Europe and the USA, in *Meningococcal disease*, Cartwright, K. (ed), John Wiley & Sons Ltd., pp. 147–157). Despite antimicrobial therapy, mortality rates in Europe and in the USA from meningococcal disease remain high (i.e., 12 to 14 percent of cases, Jafari, supra and Jones, supra.) In most industrialized countries, the vast majority of isolates causing meningococcal disease are serogroups B or C (Jones, supra; Harrison, L. (1995) *JAMA* 273:419–421; Jackson et al. (1995) *JAMA* 273:383–389; Whalen et al. (1995) *JAMA* 273:390–394). For reasons that are unknown, serogroup A strains, the major cause of disease in developing countries (Harrison, supra) are very rare in industrialized countries.

A substantial portion of meningococcal disease is potentially preventable by vaccination (Artenstein et al. (1970) *N. Engl. J. Med.* 282:417–420; Reingold et al. (1985) *Lancet* 2:114–118; Peltola et al. (1977) *N. Engl. J. Med.* 297:686–691). Effective polysaccharide vaccines against disease caused by serogroup A and C strains have been available for more than 20 years and, more recently, tetravalent vaccines have been licensed for prevention of serogroups A, C, Y and W135 isolates (Armand et al. (1982) *J. Biol. Stand.* 10:335–339; Arnbrosch et al. (1983) *Bull. World Health Organ.* 61:317–323).

Despite their general availability, meningococcal polysaccharide vaccines are used infrequently in industrialized societies (Harrison, supra). For example, in the United States, vaccination is largely limited to certain high risk situations, such as with patients with functional asplenia or terminal complement deficiency diseases (Jafari, supra). Vaccination is also used for controlling meningococcal disease in military recruits (Harrison, supra), and may be beneficial for healthy individuals traveling to hyperendemic areas, and for control of civilian outbreaks of meningococcal disease caused by serogroup strains included in the available vaccines (Perkins, supra; Masterton et al. (1988) *J. Infect.* 17:177–182). The reasons for the limited use of meningococcal polysaccharide vaccines in the general population include their poor immunogenicity in infants less than 2 years of age, the age group at greatest risk of developing meningococcal disease (Jafari, supra; Jones, supra) In addition, the duration of vaccine-induced protection elicited in older children and adults is limited (Zangwill et al. (1994) *J. Infect. Dis.* 169:847–852). Finally, these polysaccharide vaccines provide no protection against disease caused by serogroup B strains, which accounts for approximately 40% of all cases in the United States (Jafari, supra) and Canada (Whalen, supra), and an even greater proportion in the United Kingdom (Jones, supra).

More effective polysaccharide-protein conjugate vaccines for prevention of disease caused by meningococcal A and C strains are currently under development (reviewed in Granoff et al. (1997) *Int. J. Infect. Dis.* 1:152–157). These conjugate vaccines are immunogenic in infants and toddlers, and elicit high titers of serum bactericidal antibody (Fairley (1996) *J. Infect. Dis.* 174:1360–1363, and Lieberman et al. (1996) *JAMA* 275:1499–1503).

In addition, polysaccharide derivatives have been prepared to circumvent disease caused by meningococcal B strains. For example, $C_4$–$C_8$ N-acyl-substituted polysaccharide derivatives have been described. See, EP Publication No. 504,202 B, to Jennings et al. Similarly, U.S. Pat. No. 4,727,136 to Jennings et al. describes an N-propionylated meningococcal B polysaccharide molecule. Mice immunized with glycoconjugates formed with these polysaccharide derivatives were reported to elicit high titers of IgG antibodies. Jennings et al. (1986) *J. Immunol.* 137:1708. More recently, meningococcal B oligosaccharide derivative fragments, and glycoconjugates made from those fragments, have been shown to be highly effective immunogens for use in anti-meningococcal B vaccine preparations. International Publication No. WO 98/086543.

Although anti-meningococcal conjugate vaccine preparations are more effective than unconjugated vaccines in infants and toddlers, unconjugated polysaccharide vaccines are highly immunogenic in adults, eliciting effective short-term protection against disease (Artenstein, supra., Gold et al. (1971) *Bull. World Health Organ.* 45:279–282). Thus, there appears to be no real advantage to using the more costly meningococcal conjugate vaccine in adults. Indeed, in comparative immunogenicity studies, the magnitude of the serum antibody response of adults given a dose of unconjugated pneumococcal or meningococcal polysaccharide vaccine appears to be similar to that elicited by the corresponding polysaccharide-protein conjugate vaccine (Anderson et al. (1994) *Infect. Immun.* 62:3391–3395; Powers et al. (1996) *J. Infect. Dis.* 173:1014–1018).

SUMMARY OF THE INVENTION

It is a primary object of the invention to provide a method for boosting in an adult subject an immune response against meningococcal capsular antigen. The method generally entails the steps of (a) administering a first vaccine composition to an adult subject in order to elicit an immune response against a meningococcal species, and (b) administering a second vaccine composition to said adult subject in order to boost the anti-meningococcal response. The first vaccine composition comprises a meningococcal oligosaccharide conjugated to a carrier molecule, wherein the composition is administered in an amount sufficient to elicit an anti-meningococcal immune response, and said immune response is boostable upon revaccination with a second meningococcal vaccine composition. The second vaccine composition is administered to the subject after serum anti-meningococcal antibody concentration induced by the first vaccine composition have declined to subprotective levels.

It is also an object of the invention to provide a use of a first and second meningococcal polysaccharide or oligosaccharide composition in the preparation of a medicament. The first composition comprises a meningococcal oligosaccharide conjugated to a carrier molecule, and is administered in an amount sufficient to elicit an anti-meningococcal immune response which is boostable upon re-vaccination with a second meningococcal vaccine composition. The second composition comprises a meningococcal polysaccharide or oligosaccharide immunogen, and is administered to the subject after serum anti-meningococcal antibody concentrations induced by the first vaccine composition have declined to sub-protective levels.

It is an advantage of the present invention that the methods and uses can be employed in an anti-meningococcal vaccination protocol which avoids problems associated with induction of immunological tolerance to meningococcal immunogens as seen with prior vaccination strategies.

It is also a feature of the present invention that a wide variety of commonly available anti-meningococcal capsular oligosaccharide or polysaccharide glycoconjugates may be used as the immunogen in the first vaccine composition.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

Figure 1:
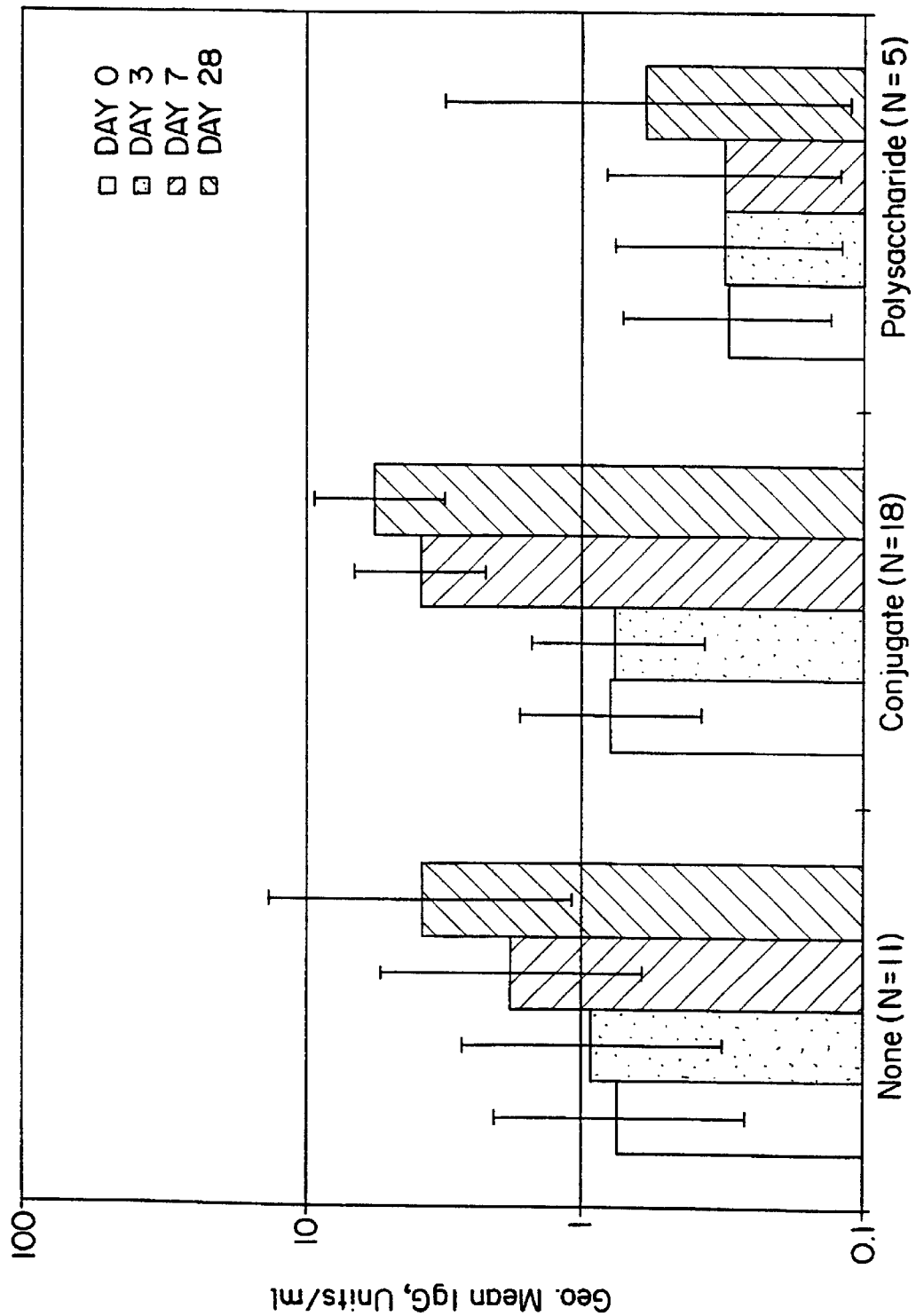
FIG. 1 depicts the geometric mean antibody response to a booster dose of the quadravalent meningococcal A, C, Y, W135 polysaccharide vaccine (MENOMUNE™) in naive subjects, and in subjects previously given either (a) a full dose of the tetravalent meningococcal polysaccharide vaccine (MENOMUNE™), or (b) a dose of an investigational meningococcal A and C oligosaccharide-protein conjugate vaccine.

The practice of the present invention will employ, unless otherwise indicated, conventional methods of immunology, microbiology, molecular biology and recombinant DNA techniques within the skill of the art. Such techniques are explained fully in the literature. See, e.g., Sambrook, et al. *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984); and *Handbook of Experimental Immunology*, Vols. I–IV (D. M. Weir and C. C. Blackwell eds., 1986, Blackwell Scientific Publications).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

I. Definitions

In describing the present invention, the following terms will be employed, and are intended to be defined as indicated below.

An "antigen" is defined herein to include any substance that may be bound by an antibody molecule. An "immunogen" is an antigen that is capable of initiating lymphocyte activation resulting in an antigen-specific immune response. Such activation generally results in the development of a secretory, cellular and/or antibody-mediated immune response against the immunogen. Usually, such a response includes but is not limited to one or more of the following effects; the production of antibodies from any of the immunological classes, such as IgA, IgD, IgE, IgG or IgM; the proliferation of B and T lymphocytes; the provision of activation, growth and differentiation signals to immunological cells; expansion of helper T cell, suppressor T cell, and/or cytotoxic T cell and/or γδ T cell populations. Immunogens therefore include any molecule which contains one or more antigenic determinants (e.g., epitopes) that will stimulate a host's immune system to initiate such an antigen-specific response.

By "epitope" is meant a site on an antigen to which specific B cells and T cells respond. The term is also used interchangeably with "antigenic determinant" or "antigenic determinant site." A peptide epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art. See, e.g., Geysen et al. (1984) *Proc. Natl. Acad. Sci. USA* 81:3998 (general method of rapidly synthesizing peptides to determine the location of immunogenic epitopes in a given antigen); U.S. Pat. No. 4,708,871 (procedures for identifying and chemically synthesizing epitopes of antigens); and Geysen et al. (1986) *Molecular Immunology* 23:709–715 (technique for identifying peptides with high affinity for a given antibody). Antibodies that recognize the same epitope can be identified in a simple immunoassay showing the ability of one antibody to block the binding of another antibody to a target antigen.

As used herein, "treatment" refers to any of (i) prevention of infection or reinfection, as in a traditional vaccine, (ii) reduction or elimination of symptoms, and (iii) reduction or complete elimination of the pathogen in question. Treatment may be effected prophylactically (prior to infection) or therapeutically (following infection).

By "mammalian subject" is meant any member of the class Mammalia, including, without limitation, humans and other primates, including such non-human primates as chimpanzees and other apes and monkey species; farm animals such as cattle, sheep, pigs, goats and horses; domestic mammals such as dogs and cats; and laboratory animals including rodents such as mice, rats and guinea pigs. The term does not denote a particular age or sex. Thus, both adult and newborn individuals, as well as fetuses, either male or female, are intended to be covered.

II. Modes of Carrying Out the Invention

The present invention is premised, in part, on the unexpected discovery that use of an anti-meningococcal conjugate vaccine composition in adults (instead of an unconjugated anti-meningococcal polysaccharide vaccine) induces polysaccharide-responsive memory B cells and long-term immunologic memory in vaccinated subjects, both of which factors contribute to more robust and durable protection against meningococcal disease. In fact, it has surprisingly been found that the anti-meningococcal immune response in adults vaccinated with a conjugate vaccine formulation is readily boostable upon re-vaccination with a second anti-meningococcal vaccine composition.

In contrast, it has also been found herein that vaccination with an unconjugated tetravalent meningococcal A, C, Y, W135 polysaccharide vaccine (MENOMUNE™, Connaught Laboratories, Inc., Swiftwater, Pa.) induces immunologic paralysis of toddlers and adults to meningococcal polysaccharides. More particularly, meningococcal C vaccination with a polysaccharide vaccine (unconjugated) in subjects during the first six months of age results in depression of serum antibody responses to a booster vaccination with meningococcal C polysaccharide given 6 months later (when compared to the responses of infants of similar age vaccinated for the first time). In the study described hereinbelow, infants were given two doses of a meningococcal A and C polysaccharide vaccine at 3 and 6 months of age and boosted with a third injection at 18 to 24 months of age. As shown in FIG. 1, the geometric mean antibody response to the booster dose was nearly 10-fold lower than that of control children of the same age vaccinated for the first time. This new information on induction of immunologic tolerance in these vaccinated subjects indicates that such tolerance is not limited to infants less than 6 months of age, but also occurs in toddlers vaccinated at 15 to 23 months, and in adults. In fact, antibody refractoriness in adult subjects was observed 4 years after a polysaccharide vaccination.

The induction of immunologic tolerance to meningococcal species in previously vaccinated subjects is of significant clinical importance. In this regard, data from experimental animals indicate that mice tolerized to pneumococcal polysaccharide show increased lethality from experimental challenge with pneumococci possessing the homologous serotype (reviewed in Halliday, W. (1971) *Bacteriol. Rev.* 35:267–289). This increased susceptibility may be a result of an impaired ability to mount serum anticapsular antibody responses upon exposure to the encapsulated bacteria. In humans, the contemporary knowledge accepts that unconjugated meningococcal polysaccharide vaccine are protective in adults and, possibly, in older children. However, this knowledge is generally based upon efficacy data in adults that were obtained from studies performed in military recruits in which follow-up was very short (8 weeks). As has been discovered herein, there may be a late-onset increased risk of disease in vaccinated subjects as a result of immune refractoriness to meningococcal polysaccharides, once increased serum antibody concentrations induced by vaccination have declined to sub-protective levels (i.e., after about 3 years). The impaired meningococcal C serum bactericidal antibody responses of toddlers and adults previously vaccinated with the tetravalent polysaccharide vaccine is consistent with this possibility.

Taken together, the data presented herein raise a safety concern for the use of unconjugated anti-meningococcal vaccines, as this product is recommended in the United States for use in children two years of age or older, but the vaccine also can be used in infants and younger children to control outbreaks of disease (Jafari, supra and Perkins, supra).

Accordingly, it is a primary object of the invention to provide a method for boosting in an adult subject an anti-meningococcal immune response against a meningococcal capsular polysaccharide antigen. The method generally entails a primary vaccination using a anti-meningococcal glycoconjugate vaccine composition which comprises meningococcal capsular polysaccharide antigen derived from one or more meningococcal species (i.e., a monovalent or polyvalent vaccine composition) conjugated to an appropriate carrier molecule. The primary vaccination is sufficient to elicit an anti-meningococcal immune response in the vaccinated subject which is specific for one or more meningococcal species. After the immune response elicited by the primary vaccination has declined to subprotective levels, a boosting vaccination is performed in order to provide a boosted anti-meningococcal immune response.

The anti-meningococcal glycoconjugates used for the primary vaccination are prepared using carrier molecules that will not themselves induce the production of harmful antibodies. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Preferably, capsular meningococcal polysaccharide or oligosaccharide molecules containing at least one immunologically relevant epitope are conjugated to a bacterial toxoid carrier molecule, such as, but not limited to, a toxoid from diphtheria, tetanus, cholera, etc. In particular embodiments, capsular polysaccharide molecules are coupled to the $CRM_{197}$ protein carrier. The $CRM_{197}$ carrier is a well-characterized non-toxic diphtheria toxin mutant that is useful in glycoconjugate vaccine preparations intended for human use. (Bixler et al. (1989) *Adv. Exp. Med. Biol.* 251:175, and Constantino et al. (1992) Vaccine). In other embodiments, glycoconjugates are formed with protein carriers known to have potent T-cell epitopes. Exemplary carriers include, but are not limited to, Fragment C of tetanus toxin (TT), and the Class 1 or Class 2/3 OMPs of *N. meningitidis*. Such carriers are well known to those of ordinary skill in the art.

In particular embodiments of the invention, the primary vaccination entails administration of a meningococcal A and C oligosaccharide-based glycoconjugate vaccine composition as described by Anderson et al. (supra). In other related embodiments, the primary vaccination is given using a meningococcal B oligosaccharide-based glycoconjugate as described in International Publication No. WO 98/086543, which publication is incorporated herein by reference in its entirety. Other vaccine compositions that can be used herein for the primary vaccination include, for example, glycoconjugates based on meningococcal B polysaccharide derivatives (e.g., those described in EP Publication No. 504,202 B and U.S. Pat. No. 4,727,1361 both of which are incorporated herein by reference), and monovalent meningococcal C or trivalent meningococcal A, B and C oligosaccharide-based glycoconjugates.

The secondary (boosting) vaccination can be carried out using any suitable anti-meningococcal vaccine composition; however, the second vaccine composition is preferably also a meningococcal capsular polysaccharide- or oligosaccharide-based conjugate in order to avoid the possibility of immunologic tolerance associated with unconjugated anti-meningococcal vaccine compositions.

As will be known by those skilled in the art upon reading the instant specification, several factors will have an impact on the physical and immunological properties of the above-described glycoconjugates. Specifically, the ratio of oligosaccharide (and/or polysaccharide)-to-protein (hapten loading density), linkage chemistry, and the choice of carrier moiety are all factors that should be considered and optimized in the preparation of the glycoconjugates used in the methods herein. For example, a low saccharide loading density may result in poor anti-saccharide antibody response. On the other hand, a heavy loading of saccharides could potentially mask important T-cell epitopes of the protein molecule, thus abrogating the carrier effect and attenuating the total anti-saccharide immune response.

Accordingly, during glycoconjugate production, aliquots can be withdrawn and analyzed by SEC-HPLC in order to monitor the extent of the conjugation process. The use of a disaggregating buffer, for example EDTA, SDS, deoxycholate, or the like, can be employed to separate components possibly adhering to the preparations by non-covalent interactions. To ensure glycosylation of the carrier, the shift in retention time of the particular protein carrier toward the exclusion volume ($V_0$) of the column can be monitored. In addition, a gradual reduction of the saccharide peak area in a HPLC chromatogram can be used to indicate incorporation of the saccharide onto the carrier.

Post-production characterization of the glycoconjugates can include molecular weight determination using, for example, gel filtration columns. Further characterization may also include electrophoretic mobility on SDS-PAGE separation equipment and analysis of chemical composition of the glycoconjugates with respect to carbohydrate and amino acid components. The identity of product purity, and the absence of residual contaminants (such as nucleic acids, LPS, and free saccharides and/or carrier) can also be verified using known techniques. Confirmation of stable covalent attachment can be accomplished using a combination of analytical techniques, including gel filtration in detergent-containing buffer, SDS-PAGE followed by Western Blot analysis and amino acid analysis. See, e.g., Vella et al. (1992) *Vaccines: New Approaches to Immunological Problems*, (Ellis, R. W. ed), Butterworth-Heinemann, Boston, pp 1–22, Seid et al. (1989) *Glycoconjugate J.* 6:489.

The anti-meningococcal vaccine compositions used in the primary and subsequent (boosting) vaccinations can further be administered in conjunction with other antigens and immunoregulatory agents, for example, immunoglobulins, cytokines, lymphokines, and chemokines, including but not limited to IL-2, modified IL-2 (cys125→ser125), GM-CSF, IL-12, γ-interferon, IP-10, MIP1β and RANTES.

The vaccine compositions will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

Adjuvants may also be used to enhance the effectiveness of the vaccines. Adjuvants can be added directly to the vaccine compositions or can be administered separately, either concurrently with or shortly after, administration of the vaccines. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (DETOX™); (3) saponin adjuvants, such as STIMULON™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

Typically, the vaccine compositions are prepared as injectables, either as liquid solutions or suspensions; or as solid forms suitable for solution in, or suspension in, liquid vehicles prior to injection. The preparation also may be emulsified or encapsulated in liposomes for enhanced adjuvant effect.

The vaccine compositions will comprise a therapeutically effective amount of one or more meningococcal capsular oligosaccharide or polysaccharide immunogens, and any other of the above-mentioned components, as needed. By "therapeutically effective amount" is meant an amount of a molecule which will induce an immunological response in the individual to which it is administered without stimulating an autoimmune response. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδ T cell populations.

Preferably, the effective amount is sufficient to bring about treatment, i.e., reduction or complete elimination of symptoms, or prevention of disease symptoms. The exact amount necessary will vary depending on the subject being treated; the age and general condition of the subject to be treated; the capacity of the subject's immune system to synthesize antibodies; the degree of protection desired; the severity of the condition being treated; the particular molecule selected and its mode of administration, among other factors. An appropriate effective amount can be readily determined by one of skill in the art. A "therapeutically effective amount" will fall in a relatively broad range that can be determined through routine trials. More particularly, the meningococcal capsular oligosaccharide or polysaccharide immunogens will be administered in a therapeutically effective amount that comprises from about 0.1 μg to about 100 mg, more preferably from about 0.5 μg to about 1 mg, and most preferably about 1 μg to about 500 μg of the oligosaccharide or polysaccharide immunogen delivered per dose.

Once formulated, the vaccine compositions are conventionally administered parenterally, e.g., by injection, either subcutaneously or intramuscularly. Alternative formulations suitable for other modes of administration include oral and pulmonary formulations, suppositories, and transdermal applications. Dosage treatment may be a single dose schedule or a multiple dose schedule.

III. Experimental

The following studies were designed to assess whether meningococcal conjugate vaccination of adults induces immunologic memory to unconjugated meningococcal C polysaccharide. To address this question, adults who had been immunized three to four years earlier with an investigational meningococcal A and C conjugate vaccine were re-vaccinated with unconjugated tetravalent meningococcal polysaccharide vaccine. The serum antibody responses to this booster injection were compared to those of previously unvaccinated adults, or those of adults previously vaccinated with unconjugated meningococcal polysaccharide vaccine. Since "unprimed" adults were expected to show very high serum antibody responses to unconjugated meningococcal polysaccharide vaccine, the dose of meningococcal polysaccharide vaccine that was used for the booster injection was chosen such that it would normally be considered suboptimally immunogenic (1/50 of the usual dose, to serve as a probe of B cell immunologic memory).

A. Methods

Subjects: The following study was approved by the Saint Louis University Institutional Review Board. Thirty-four healthy adults, ages 20 to 53 years, were divided into three groups based on their previous meningococcal vaccination histories. Group 1 consisted of 5 subjects, each of whom had received a full dose of a U.S. licensed tetravalent meningococcal polysaccharide vaccine (MENOMUNE™, 50 μg of A, C, Y, and W135 polysaccharides per 0.5 ml dose). This dose was given four years earlier as part of a previous study (Anderson, supra). Group 2 consisted of 18 subjects who had received a dose of an investigational meningococcal A and C oligosaccharide-protein conjugate. Fifteen of these subjects had been immunized four years earlier as part of the same study (Anderson, supra). The remaining three subjects were vaccinated three years earlier in a subsequent trial (Anderson et al., unpublished data).

The conjugate vaccine used in the studies contained 22 μg each of Group A and C oligosaccharides and 48.7 μg of $CRM_{197}$ protein (a cross-reactive mutant nontoxic diphtheria toxin). Four of the subjects in group 2 received the full 22 μg dose, 11 received an 11 μg dose (including the three subjects vaccinated in the second trial), and 3 received a 5.5 μg dose. All doses were adsorbed to 1 mg of aluminum hydroxide and given in a 1 ml dose. In the present study, the magnitude and kinetics of the booster antibody responses of the subjects previously given different doses of conjugate vaccine were very similar. Therefore, for presentation of the results, the data from the three priming doses were combined. Group 3 consisted of 11 adults who had not previously received meningococcal vaccine. Two of the subjects in this group had been randomized in the first study to receive a saline placebo injection (Anderson, supra), and the remaining 9 subjects were previously unvaccinated healthy adults recruited as controls for the present booster study.

The demographic characteristics of the three "priming" vaccine groups were similar with respect to median age at the time of the booster vaccination (38, 36, and 40 years of age for groups 1, 2, and 3, respectively), gender (predominantly female: 100%, 89%, and 82%, respectively), and race distribution (white: 100%, 94%, and 91%, respectively).

Vaccinations: After informed consent, all 34 healthy adults in groups 1, 2 and 3 were vaccinated with 1/50 of the usual dose of a quadravalent meningococcal A, C, Y, and W135 polysaccharide vaccine (1 ml containing 1 μg of each polysaccharide, given IM in the deltoid). To prepare this dose, lyophilized meningococcal polysaccharide vaccine (MENOMUNE™) from Connaught Laboratories (Swiftwater, Pa., U.S.) was reconstituted with 0.6 ml of diluent provided by the manufacturer. The resulting solution contained 100 μg/ml of each of the polysaccharides. From this solution, 0.5 ml was diluted into 49.5 ml of preservative-free saline for injection, to yield the 1 ml dose. Serum samples were obtained immediately prior to vaccination (time 0), and 3, 7 and 28 days later, for measurement of antibody response to the meningococcal C component of the vaccine.

Immunoassays: All assays were performed "blindly" on coded serum samples. Serum anti-*N meningitidis* group C polysaccharide antibody concentrations were measured by an enzyme-linked immunosorbent assay (ELISA), adapted from a method previously described (Granoff et al. (1997) *Infect. Immun.* 65:1710–1715). In the present study, the assay employed an alkaline-phosphatase conjugated mouse monoclonal antibody specific for human IgG (clone HP6083) (Granoff et al. (1995) *Clin. Diagn. Lab. Immunol.* 1:574–582). Also, the buffer for diluting the serum samples contained 75 mM sodium thiocyanate, which favored the detection of high avidity anticapsular antibodies as compared to low avidity antibodies (Raff et al. (1996) "Correlation between ELISA and bactericidal activity in infants and toddlers immunized with a MenC-CRM conjugate vaccine," in Abstracts of the 36th *Interscience Conference on Antimicrobial Agents and Chemotherapy*, page 158 (Abstract)). The IgG meningococcal C anticapsular antibody concentrations in test samples are reported in arbitrary units per ml, compared to that present in an internal reference serum pool prepared from serum samples from vaccinated healthy adults. For comparison, the meningococcal reference serum pool CDC1992 (provided by George Carlone, Centers for Disease Control and Prevention, Atlanta, Georgia) (Gheesling et al. (1994) *J. Clin. Microbiol.* 32:1475–1482) contained 19.1 units/ml of the meningococcal C anticapsular antibody as measured by this modified assay.

Complement-mediated bactericidal antibody to *Neisseria meningitidis* group C was assayed as previously described, (Granoff et al. (1997) *Infect. Immun.* 65:1710–1715; and Mandrell et al. (1995) *J. Infect. Dis.* 172:1279–1289) with the following modifications. The group C test organism (*N. meningitidis* group C, strain 60E, obtained from Dr. W. Zollinger, Walter Reed Institute for Medical Research, Washington, D.C.) was grown for approximately 2 hours in Mulleur Hinton (MH) broth containing 0.25% glucose, which rendered the organism resistant to complement-mediated bacteriolysis by endogenous "natural" antibodies, as compared to organisms grown in Mulleur Hinton without supplemental glucose. All test sera were heated at 56° C. for 30 mins to inactivate endogenous complement. The complement source for the bactericidal assay was pooled sera obtained from three healthy adults who had no detectable anticapsular antibody to meningococcal C, and whose sera lacked intrinsic bactericidal activity when tested at 40 percent. In the bactericidal assay, this complement source was used at 20 percent in the final reaction mixture, along with serial 2-fold dilutions of test sera beginning at a 1:8 dilution (12.5 percent in the final reaction) and Gey's buffer (instead of barbital buffer as previously described) (Mandrell, supra). Serum bactericidal titers were defined as the dilution of test sera resulting in a 50% decrease in colony forming units per ml after 60 minutes incubation of bacteria in the reaction mixture, compared to control bacteria at time 0. Note that the titers reported with this assay tend to be lower than those described in previous studies (Anderson, supra and Maslanka et al. (1997) *Clin. Diagn. Lab. Immunol.* 4:156–167). The principal reasons are: (1) the use of a test organism grown with supplemental glucose; (2) the use of Gey's buffer instead of barbital buffer (Mandrell, supra) and (3) the use of human as opposed to rabbit complement, since in previous studies rabbit complement was shown to amplify greatly bactericidal activity of human antibodies (Mandrell, supra and Zollinger et al. (1983) *Infect. Immun.* 40:257–264). Human complement also was chosen for the present study because the data demonstrating that serum bactericidal antibody correlated with protection of humans against invasive meningococcal disease were derived from studies that used human complement (Goldschneider et al. (1969) *J. Exp. Med.* 129:1307–1326).

Statistical analysis: Antibody concentrations were transformed ($\log_{10}$). For these calculations, bactericidal titers less than 1:8 were assigned as 1:4, and IgG antibody concentrations less than 0.4 units/ml were assigned a value of 0.2 units/ml. Geometric means and 95% confidence intervals were computed by using the log transformed means and standard errors were computed from a one-way analysis of variance (ANOVA) model. Differences between each pair of groups with respect to geometric means were tested by using the P values from the ANOVA model.

B. Results

Clinical tolerability: Vaccination with 1/50 of the usual dose of MENOMUNE™ was well tolerated irrespective of previous meningococcal vaccination status. During the 28 days of follow-up, there were no clinically significant local reactions at the injection site or systemic reactions, such as fever, rash, or myalgia, in any of the 34 subjects.

Antibody response: FIG. 1 shows the geometric mean IgG anticapsular antibody responses of each group to the booster vaccination. Prior to the vaccination, there were no significant differences between the geometric mean antibody concentrations of the three groups (0.30, 0.78 and 0.73 units/ml, for groups 1, 2, and 3, respectively). At 3 days after vaccination, there was no evidence of a significant increase in serum IgG antibody concentrations in any of the groups, when compared to the respective antibody concentrations present in pre-vaccination sera. However, by 7 days, subjects in group 2, who previously had received the conjugate vaccine, and subjects in group 3, who were vaccinated for the first time, showed significant IgG responses, compared to their respective IgG serum antibody concentrations present at time 0 ($p<0.05$ for each group). In contrast, the adults in group 1, who had received a full dose of licensed meningococcal A and C polysaccharide vaccine 4 years earlier, showed no evidence of an IgG response at 7 days (geometric mean IgG antibody concentration of 0.38 units/ml at 7 days vs. 0.42 units/ml at time 0). Similarly, there was no significant increase in geometric mean antibody concentration in this group when measured at 28 days (0.68 units/ml, $P>0.5$). At 28 days, only one subject in group 1 showed a $\geq$4-fold increase in IgG antibody concentration, and the respective geometric mean IgG antibody responses were 6- to 10-fold lower than those of groups 2 or 3 ($p<0.003$ at 7 days; and $p<0.01$ at 28 days).

Table 1, below, summarizes the bactericidal antibody responses of the three groups as measured in serum samples obtained at time 0, and 7 and 28 days after the booster vaccination (bactericidal assays were not performed in the sera obtained at 3 days). Prior to the booster vaccination, all five subjects in group 1 had titers less than 1:8 (undetectable), and the majority of adults in groups 2 and 3 also had undetectable bactericidal titers (Table 1). Following vaccination, the geometric mean bactericidal antibody responses at 7 and 28 days paralleled the respective IgG antibody responses. Specifically, at 7 days there was no evidence of an increase in bactericidal antibody titers in group 1, compared to the respective pre-vaccination titers, and the GMT of group I at 7 days was 10- to 25-fold lower than the respective GMTs of groups 2 or 3 ($p<0.001$). At 28 days, similar respective differences were present ($P<0.006$). Further, at 28 days, the proportion of subjects with bactericidal titers $\leq1:8$ was only 20% in group 1, vs. 100% for group 2 ($P=0.01$), vs. 64% for Group 3 ($P=0.11$).

TABLE 1

Complement-Mediated Bactericidal Antibody Responses of Adults to a Meningococcal Polysaccharide Booster Immunization*

| Group | Meningococcal Priming Vaccine | No. Tested | Geometric Mean (Reciprocal Titer) ±95% Confidence Interval | | | Percent with Titer $\geq$ 1:8 | | |
|---|---|---|---|---|---|---|---|---|
| | | | Pre- | 7 Days Post | 28 Days Post | Pre- | 7 Days Post | 28 Days Post |
| 1 | Polysaccharide | 5 | 4.0 (4–4) | 4.9 (2.8–8.6) | 8.5 (1.1–68) | 0 | 20 | 20 |
| 2 | Conjugate | 18 | 9.3 (4–21) | 136 (69–268) | 200 (108–371) | 22 | 100 | 100 |
| 3 | Unvaccinated | 11 | 9.2 (3.4–25) | 43 (11–174) | 88 (17–463) | 36 | 64 | 73 |

*For the booster injection, all subjects were given 1/50th of the usual dose of Menomune (1 μg of each polysaccharide, IM).
Statistical Analysis: The group previously given Menomune showed no significant antibody response to the booster. Comparing GMTs of the 3 groups at each time point (Pre, p = 0.5; 7 days, p < 0.001; and 28 days, p = 0.005). Pair-wise comparisons between GMTs of group previously vaccinated with Menomune vs. unvaccinated: 7 days, p = 0.01; and 28 days p = 0.02). Pair-wise comparisons between GMTs of group previously vaccinated with conjugate vaccine vs. unvaccinated: 7 days, p = 0.06; and 28 days, p = 0.24. Pair-wise comparisons of percent with titers $\geq$ 1:8 between group previously vaccinated with conjugate vs. unvaccinated: 7 days, p < 0.02; and 28 days, p < 0.05 (by Chi square analysis).

The principle finding of this study is that four years after immunization with meningococcal polysaccharide vaccine, healthy adults show much lower anti-meningococcal C serum antibody responses to a booster injection with 1/50th of the usual dose of meningococcal polysaccharide vaccine than adults vaccinated for the first time. In contrast, the magnitude of the booster responses of adults previously vaccinated with an investigational meningococcal conjugate vaccine was similar or higher than that of the adults vaccinated for the first time. These data are consistent with induction of immunologic tolerance to meningococcal C polysaccharide by the prior vaccination with the licensed polysaccharide vaccine, but not by the investigational conjugate vaccine. The conclusion that the initial unconjugated polysaccharide vaccination in adults induced immunologic tolerance is based on the booster responses of 5 subjects, wherein the magnitude of the impairment found was very large (10-fold), and thus unlikely to have resulted from chance alone ($P\leq0.01$).

One contributing factor in the mechanism for the above-described induction of immunologic tolerance may be the relatively high dose of polysaccharide used in the licensed meningococcal vaccine (50 μg). That this dose may be excessive is suggested by the excellent immunogenicity of a 1 μg dose in the control adults immunized in the present study for the first time (FIG. 1 and Table 1). Also, in a previous study in infants, impaired booster antibody responses to meningococcal C polysaccharide were observed only after vaccination with 25 μg or 100 μg of vaccine, but not after a 10 μg dose (Goldschneider et al. (1973) *J. Infect. Dis.* 128:769–776). In mice, large doses of polysaccharide antigens also have been found to induce immunologic tolerance, whereas lower doses are immunogenic and do not induce a refractory state to revaccination (reviewed in Halliday, supra) Accordingly, novel methods for boosting anti-meningococcal immune responses in adults, and uses of first and second meningococcal vaccine compositions in the preparation of medicaments are disclosed. Although preferred embodiments of the subject invention have been described in some detail, it is understood that obvious variations can be made without departing from the spirit and the scope of the invention as defined by the appended claims.

What is claimed is:

1. A method for boosting in an adult subject an immune response against meningococcal C capsular antigen, said method comprising:
   (a) administering a first vaccine composition to said adult subject in order to elicit an immune response against a meningococcal species, wherein said first vaccine composition is a meningococcal glycoconjugate vaccine composition that comprises meningococcal oligosaccharides from serogroups A and C, wherein the oligosaccharides are conjugated to a carrier molecule, and further wherein the first composition is administered in an amount sufficient to elicit an anti-meningococcal immune response; and
   (b) administering a second vaccine composition to said adult subject in order to boost the anti-meningococcal response, wherein said second vaccine composition comprises capsular polysaccharides from serogroups A, C, Y and W135, and is administered to the subject about three to four years after the first vaccine composition is administered.

2. The method of claim 1, wherein the oligosaccharides of the first vaccine composition are conjugated to a protein carrier.

3. The method of claim 2, wherein the protein carrier is $CRM_{197}$.

4. The method of claim 1, wherein the second vaccine composition comprises an unconjugated meningococcal polysaccharide.

5. The method of claim 4, wherein the second vaccine composition comprises 1 μg of each polysaccharide.

6. The method of claim 1, wherein the second vaccine composition is administered to the adult subject not less than three years after administration of the first vaccine composition.

7. A method for producing an immune response against meningococcal C capsular antigen in an adult subject, said method comprising:
   (a) administering a first vaccine composition to said adult subject in order to elicit an immune response against a meningococcal species, wherein said first vaccine composition is a meningococcal glycoconjugate vaccine composition that comprises meningococcal oligosaccharides from serogroups A and C, wherein the oligosaccharides are conjugated to $CRM_{197}$, and further wherein the first composition is administered in an amount sufficient to elicit an anti-meningococcal immune response; and
   (b) administering a second vaccine composition to said adult subject in order to boost the anti-meningococcal response, wherein said second vaccine composition comprises capsular polysaccharides from serogroups A, C, Y and W135 wherein said capsular polysaccharides are not conjugated to a carrier molecule, and further wherein said second vaccine composition is administered to the subject about three to four years after the first vaccine is administered.

8. The method of claim 7, wherein the second vaccine composition comprises 1 μg of each polysaccharide.

* * * * *